United States Patent
Burchette et al.

(10) Patent No.: US 6,398,931 B1
(45) Date of Patent: Jun. 4, 2002

(54) COMBINATION ION-SELECTIVE ELECTRODE WITH A REPLACEABLE SENSING MEMBRANE

(75) Inventors: Raymond Gary Burchette, Richmond; Dung Van Chu, Houston; Peter F. Boyle, Sugar Land, all of TX (US)

(73) Assignee: Phoenix Electrode Company, Houston, TX (US)

( * ) Notice: Subject to any disclaimer, the term of this patent is extended or adjusted under 35 U.S.C. 154(b) by 0 days.

(21) Appl. No.: 09/495,084

(22) Filed: Jan. 31, 2000

(51) Int. Cl.[7] .............................................. G01N 27/333
(52) U.S. Cl. ....................... 204/416; 204/417; 204/418; 204/419; 204/420; 204/435
(58) Field of Search ................................. 204/416, 417, 204/418, 419, 420, 435

(56) References Cited

U.S. PATENT DOCUMENTS

| | | | |
|---|---|---|---|
| 3,492,216 A | 1/1970 | Riseman et al. ............ 204/195 |
| 3,879,279 A * | 4/1975 | Baucke ........................ 204/419 |
| 4,008,141 A * | 2/1977 | Kotani et al. ................ 204/420 |
| 4,115,209 A * | 9/1978 | Freiser et al. ................ 204/418 |
| 4,152,235 A | 5/1979 | Dobson ................. 204/195 M |
| 4,182,668 A | 1/1980 | Koshiishi et al. ........ 204/195 L |
| 4,196,056 A | 4/1980 | Kumar ........................ 204/1 T |
| 4,340,457 A | 7/1982 | Kater ...................... 204/195 R |
| 4,388,167 A | 6/1983 | Ono et al. ................... 204/420 |
| 4,396,486 A | 8/1983 | Mruk et al. ................. 204/419 |
| 4,479,865 A | 10/1984 | Beder et al. ................. 204/415 |
| 4,528,085 A | 7/1985 | Kitajima et al. ............ 204/416 |
| 4,533,457 A | 8/1985 | Watanabe ................... 204/411 |
| 4,549,951 A | 10/1985 | Knudson et al. ............ 204/416 |
| 4,555,274 A | 11/1985 | Kitajima et al. ........ 148/6.14 R |
| 4,565,665 A | 1/1986 | Fogt ............................ 264/267 |
| 4,571,293 A | 2/1986 | Seshimoto et al. ......... 204/418 |
| 4,578,173 A | 3/1986 | Seshimoto et al. ......... 204/416 |
| 4,615,788 A | 10/1986 | Seshimoto et al. ......... 204/418 |
| 4,647,362 A | 3/1987 | Watanabe ................... 204/411 |
| 4,683,048 A | 7/1987 | Yamada et al. ............. 204/416 |
| 4,707,243 A | 11/1987 | Seshimoto et al. ......... 204/418 |
| 4,798,664 A | 1/1989 | Yamaguchi et al. ........ 204/418 |
| 4,981,570 A | 1/1991 | Yamaguchi et al. ........ 204/418 |
| 4,995,960 A | 2/1991 | Wiles et al. ................. 204/418 |
| 5,112,471 A | 5/1992 | Shibata et al. .............. 204/418 |
| 5,284,568 A | 2/1994 | Pace et al. ................... 204/403 |
| 5,324,414 A | 6/1994 | Spahn et al. ................ 204/416 |
| 5,344,547 A | 9/1994 | Vlasov et al. ............... 204/419 |
| 5,393,402 A * | 2/1995 | Dervaes et al. ............. 204/419 |
| 5,552,032 A * | 9/1996 | Xie et al. .................... 204/416 |
| 5,571,394 A * | 11/1996 | Hettiarachchi et al. ..... 204/400 |
| 5,629,212 A | 5/1997 | Herman et al. ............. 136/125 |
| 5,830,338 A * | 11/1998 | Seto et al. ................... 204/416 |

FOREIGN PATENT DOCUMENTS

EP      0 807 817 A1 * 11/1997

* cited by examiner

Primary Examiner—Robert J. Warden, Sr.
Assistant Examiner—Kaj K. Olsen
(74) Attorney, Agent, or Firm—Henry L. Ehrlich; Winstead Sechrest & Minick PC

(57) ABSTRACT

An improved combination ion-selective electrode apparatus is provided that comprises an electrode body, a reference electrode, and an ion-sensing electrode. The reference electrode comprises a ion-permeable junction. A removable membrane cap contains a ion-selective membrane. The membrane cap can be removed from the ion-selective electrode apparatus without endangering the integrity of the reference electrode and is distinct from the ion-permeable junction. The membrane cap contains a removable ion-sensitive membrane that can be replaced if the ion-sensitive membrane fails to thereby place the combination ion-selective electrode apparatus back into service. Moreover, a single combination ion-selective electrode apparatus can be used to measure a variety of analyte ions by simple replacement of the membrane cartridge.

33 Claims, 6 Drawing Sheets

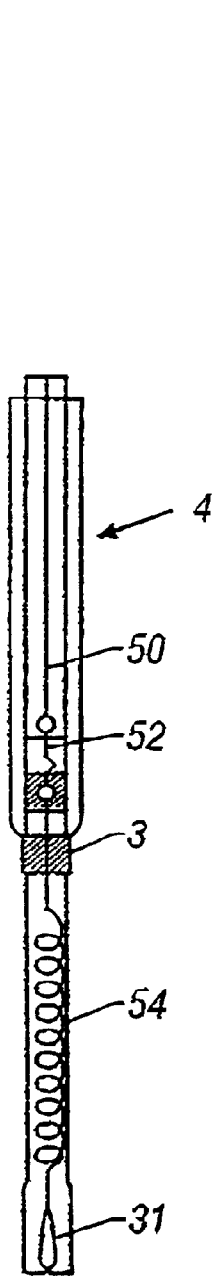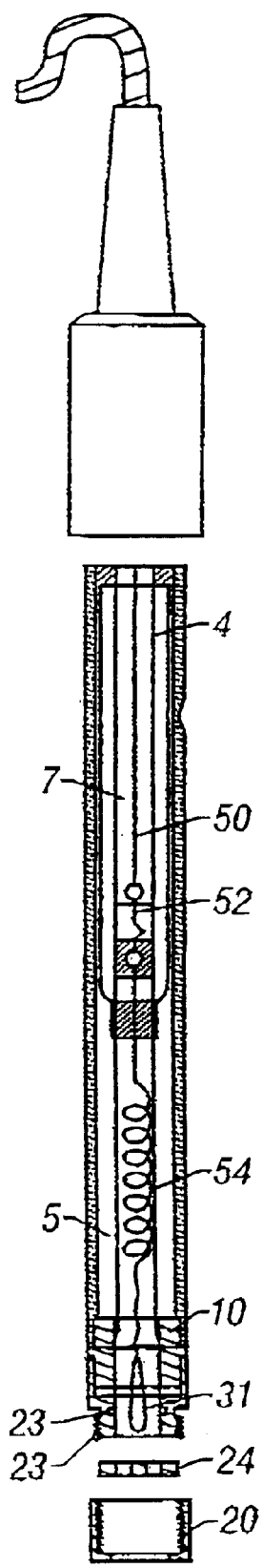
FIG. 4
FIG. 5

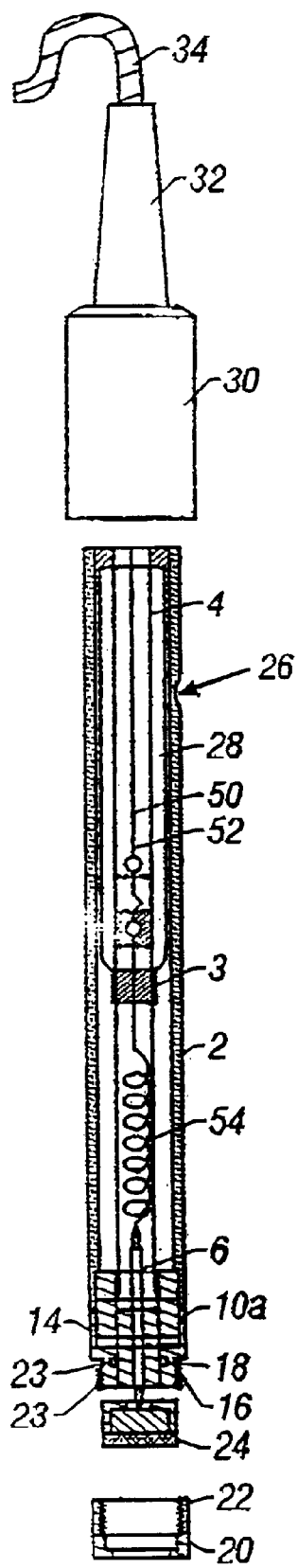
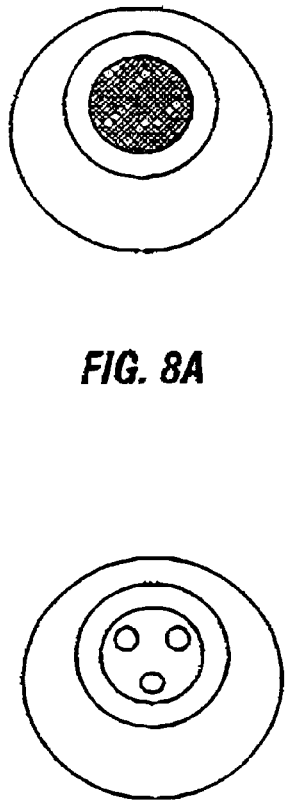
FIG. 8A
FIG. 9A
FIG. 8
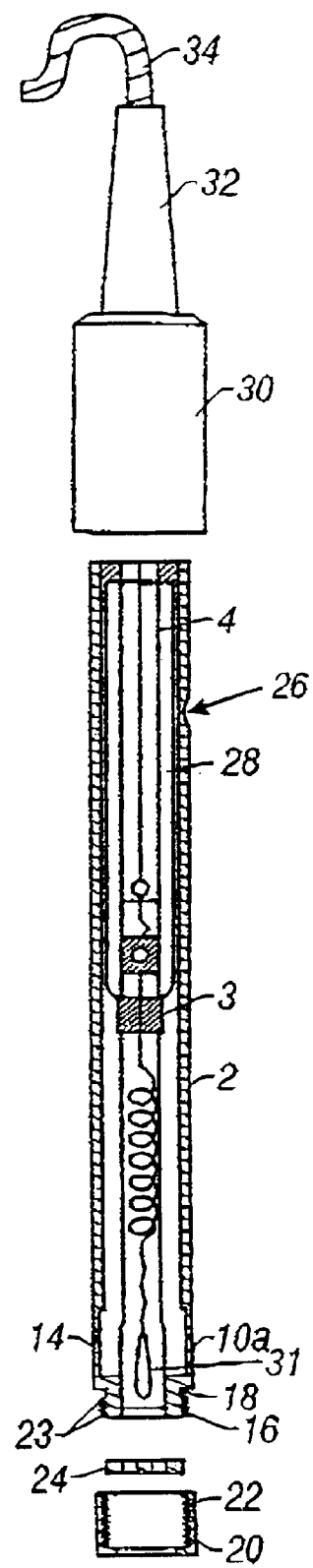
FIG. 9

COMBINATION ION-SELECTIVE ELECTRODE WITH A REPLACEABLE SENSING MEMBRANE

FIELD OF THE INVENTION

This disclosure relates to ion-selective electrodes and, more particularly, to a combination ion-selective electrode with a replaceable ion-sensing membrane.

BACKGROUND OF THE INVENTION

Ion-selective electrodes can be constructed to comprise semi-permeable membranes that separate two aqueous solutions. One solution is a reference solution having a substantially fixed concentration of ions. The other solution is a sample solution containing the ions to be detected. When the electrode is placed in contact with the sample solution, a potential develops across the membrane in accordance with the Nernst equation. This potential, or voltage, varies as a function of the concentration of the ion being detected in the sample solution.

Semi-permeable membranes suitable for ion-selective electrodes may comprise various materials. For example, certain salts of anions such as bromide, chloride, and sulfide which are highly insoluble in aqueous solution. Salt anion membranes commonly take the form of quasi-amorphous masses or highly compressed polycrystalites. Suitable membranes may also comprise massive monocrystals of rare earth fluorides for sensing fluoride ions, or they may simply be glasses known to be sensitive to, for example, hydrogen, sodium, or potassium ions. The membrane may also be formed of ion exchange material held in an inert, porous substrate. Additionally, polyvinyl chloride (PVC) and epoxy may be suitable membrane materials.

A potentiometric measurement cell comprises two half cells. Ion-selective measurement cells are potentiometric cells where one half cell is the ion-selective electrode ("ISE") and the other is a reference electrode. ISEs and reference electrodes can be constructed as separate assemblies which are then used together in a test solution to comprise an entire measuring cell. It is more common, however, to construct a single assembly or probe which combines both the reference electrode and the ISE. A probe which combines the reference and ion-selective electrodes is referred to as a combination ISE. Combination ISEs are advantageous in that they are often less expensive than a pair of individual half cell electrodes and the compact geometry of a single probe allows use of the measurement cell in smaller volumes of samples.

The reference electrode usually includes an internal reference element composed of a metal or metal-salt combination, one or two reference electrolyte solutions (salt bridge solutions), and one or two liquid junctions which are small orifices, porous barriers, or other restrictions which inhibit excessive mixing of a reference electrolyte with the sample solution, yet provides electrical contact between the reference and the sample. The ion-selective electrode incorporates a sensing membrane which is permanently sealed into the body of the electrode.

The ion-selective sensing membrane tends to have the shortest useful life of all the measurement cell components. Typically, when the ion-selective sensing membrane has expended its useful life, the membrane cannot be removed from the combination ISE because it is permanently sealed into the electrode body. Thus, the combination ISE cannot be rebuilt and must be discarded. The cost of buying a new electrode is much higher than the cost of replacing just the ion-selective sensing membrane. Moreover, the time involved in procuring a new electrode from the supplier is much greater than the time involved would be in disassembling the old electrode, replacing the membrane, and reassembling the electrode.

A half cell ion-selective electrode with a replaceable sensing membrane is known, but this half cell is not available in a combination ISE. A combination ISE with a replaceable sensing module is also known, but, as with the half-cell apparatus, the replaceable module includes an internal reference electrode element and reference electrolyte contained in chamber of the module. The replaceable module does not provide for replacing only the ion-selective membrane. The replaceable module I SE incidentally provides for replacement of the ion-selective membrane, but only together with the other elements of the module. Replacing the ion-selective membrane in a combination ISE poses different problems from replacing the membrane in an half-cell electrode. In this latter combination ISE module, the module further forms a part of the liquid junction as an annular sleeve disposed within the probe body. This modular design relies on a spring-loaded outer body seating properly on the tapered end of the bottom section of the module to control the flow rate of reference electrolyte flowing at the reference junction. Replacement of the module therefore affects the integrity of the reference junction. It would be desirable that the membrane be removable without causing the reference electrolyte to flow excessively after replacing the membrane in a combination ISE. The replaceable module is directed toward a different problem from that of the present combination ISE, and therefore does not provide a combination ISE that provides for replacement of only the ion-selective membrane. And further, the replaceable module does not provide an apparatus where the membrane replacement assembly is sequestered from the reference electrolyte so that the membrane may be replaced without disturbing the reference electrolyte solution.

The prior art also provides a cap assembly for replacing a selectively gas-permeable membrane in a non-ISE electrode. The cap assembly of this prior art comprises a housing having a port, an internal conical surface sloping away from the port, an annular groove in the conical surface, an annular O-ring type sealing element disposed in the groove, a disk-type sealing element seated on the O-ring, and a membrane securing element having a clamp element that mates with the conical surface of the housing. The assembly is suitable for detecting gases in a gaseous state that diffuse across the membrane, but is not suitable for detecting ions in an analytical sample where the ions do not diffuse across the membrane in a gaseous state. That is, the assembly of this prior art is not suitable for ISEs. One reason this prior art assembly is unsuitable for ISEs is that the assembly does not provide semi-permeable membrane with ion selective materials between the reference electrolyte solution and the analytical solution, and therefore the electrode cannot detect ions in solution in the analytical sample. The membrane itself may allow gas permeation in this prior art. However, it is undesirable for the membrane to allow ion permeation as required in an combination ISE. Another drawback of this prior art is that the cap assembly snaps on and off of the end of the electrode to replace the membrane. To remove the cap assembly for membrane replacement, one must apply torsional or axial force to the electrode body. Application of such forces to the electrode body increases the likelihood that excessive force will be applied, occasionally resulting in the destruction of the electrode body requiring replacement of the entire electrode apparatus at great expense.

The ion-sensing membrane of the combination ISE is the component that has the most exposure to external elements. This continual exposure to the external environment contributes to the short useful life of the membrane. Sample contamination, sample temperature, sample pH, sample pressure, physical abuse, membrane aging, and exposure to ultra-violet and other ambient radiation all contribute to the deterioration of the membrane. However, there is no known combination ISE which allows the user to simply replace the membrane after the membrane has expended its useful life. One must either use a half cell ion-selective electrode with a replaceable sensing membrane together with a separate reference electrode, or one must use a combination ISE where only a module comprising a membrane together with an internal reference element and internal reference electrolyte can be replaced. Those skilled in the art will appreciate the present invention that addresses these and other problems.

SUMMARY OF THE INVENTION

Therefore, a combination ISE with a replaceable ion-sensing membrane is provided. The membrane is easily replaced without sacrificing the other components of the combination ISE, achieving cost and time-saving benefits. These benefits are particularly important where continuous or frequent sample analysis is required (for example, industrial processes) and the combination ion-selective electrode may be potted in a suitable industrial housing design. The replaceable membrane provided herein does not form part of the liquid junction or salt bridge with the reference electrolyte; therefore, there is no danger of reference electrolyte leakage upon replacing the membrane. This may be contrasted against known cartridge designs where the membrane must be removed together with a reference electrolyte module and the entire cartridge is replaced on the electrode. Provided is a combination ISE where the ion-selective sensing membrane is the only removable part, and this membrane does not, in any manner, form part of the liquid junction with the reference electrolyte.

The combination ion-selective probes with replaceable sensing membranes provided herein were designed and evaluated for a wide-range of sample analytical ions, including but not limited to ammonium, bromide, cadmium, calcium, chloride, copper, cyanide, fluoride, fluoroborate, iodide, lead, magnesium, nitrate, perchlorate, potassium, silver, sulfide, and surfactant.

Probes were tested for overall performance characteristics equivalent to or better than:

comparable half cell ion-selective electrodes used with separate single or double junction reference electrodes;

overall performance characteristics equivalent to or better than comparable combination ISEs in which the sensing membrane was sealed into the body and not replaceable; and easily replaceable ISE membranes.

In one embodiment, the combination ISE provided herein comprises a sensing membrane in the form of a replaceable PVC cartridge and sealed into the combination ISE body with one or two O-rings. This replaceable PVC cartridge is designed for, but not limited to, ammonium, calcium, fluoroborate, magnesium, nitrate, perchlorate, potassium, and surfactant.

In another embodiment, the combination ISE comprises a sensing membrane in the form of a pressed pellet encased in a replaceable epoxy cartridge and sealed into the combination ISE with one or two O-rings. This replaceable epoxy cartridge is designed for, but not limited to, the following analytical ions: bromide, cadmium, chloride, copper, cyanide, iodide, lead, silver and sulfide.

In yet another embodiment, the combination ISE comprises a sensing membrane in the form of a solid crystal and is sealed into the combination ion-selective electrode body with one or two O-rings. This replaceable crystal is designed for, but not limited to the analytical ion fluoride.

One advantage of the present device is that when the sensing membrane fails or loses performance for whatever cause, it can be immediately replaced without discarding any other portion of the combination ISE. This results in time and costs savings.

Another advantage is that the membrane replacement has no unfortunate side effects on the performance of the reference electrode, whereas membrane replacement with an annular sleeve module can affect the performance of the reference electrode.

Yet another potential advantage of the present device is the option of interchangeable sensing membranes, where one can select a membrane most suitable for a particular analytical ion. A single combination ISE body can be used to measure a variety of analytical ions by simple replacement of the membrane cartridge or crystal. This offers benefits in multiple ion analysis whereby an electrode kit containing various replaceable membranes can be made available for the analysis of different determinands done on an occasional basis. The known modular designs for ISEs rely on a spring-loaded outer body, seating properly on the tapered end of the bottom section of the module to control the flow rate of the reference electrolyte flowing at the reference junction. In contrast, the combination ISE provided herein does not require any proper seating at the junction with the reference electrolyte. That is, the ion-sensitive membrane provided herein is easily replaceable without endangering the integrity of the reference electrolyte junction.

BRIEF DESCRIPTION OF THE DRAWINGS

FIG. 4—Cross-sectional side view of the internal body assembly of a PVC membrane cartridge or solid crystal membrane ISE.

FIG. 5—Cross-sectional side view of an alternative embodiment of the present combination, with a replaceable PVC membrane cartridge.

FIG. 8—Cross-sectional exploded side view of the combination ISE of FIG. 3 with ceramic wick instead of annular ceramic.

FIG. 9—Cross-sectional exploded side view of the combination ISE of FIGS. 6 and 7 with ceramic wick instead of annular ceramic.

GENERAL DESCRIPTION AND PREFERRED MODE FOR CARRYING OUT THE INVENTION

The probe of the present combination ion-selective electrodes (ISE) comprises a combination ion-selective electrode with a sensing half cell and reference half cell incorporated into one single functional probe. A desirable feature of the sensing half cell is the replaceability of the ISE material in the form of an ion-selective membrane or membrane crystal. For convenience of description in this application, as used herein "membrane cartridge" comprises various types of replaceable ion-selective membranes that may be used, by way of example and not limitation including a pressed pellet membrane, crystal membrane whether solid or non-solid, PVC membrane, epoxy membrane, and the like, or any combination thereof.

Figures 1, 1A:
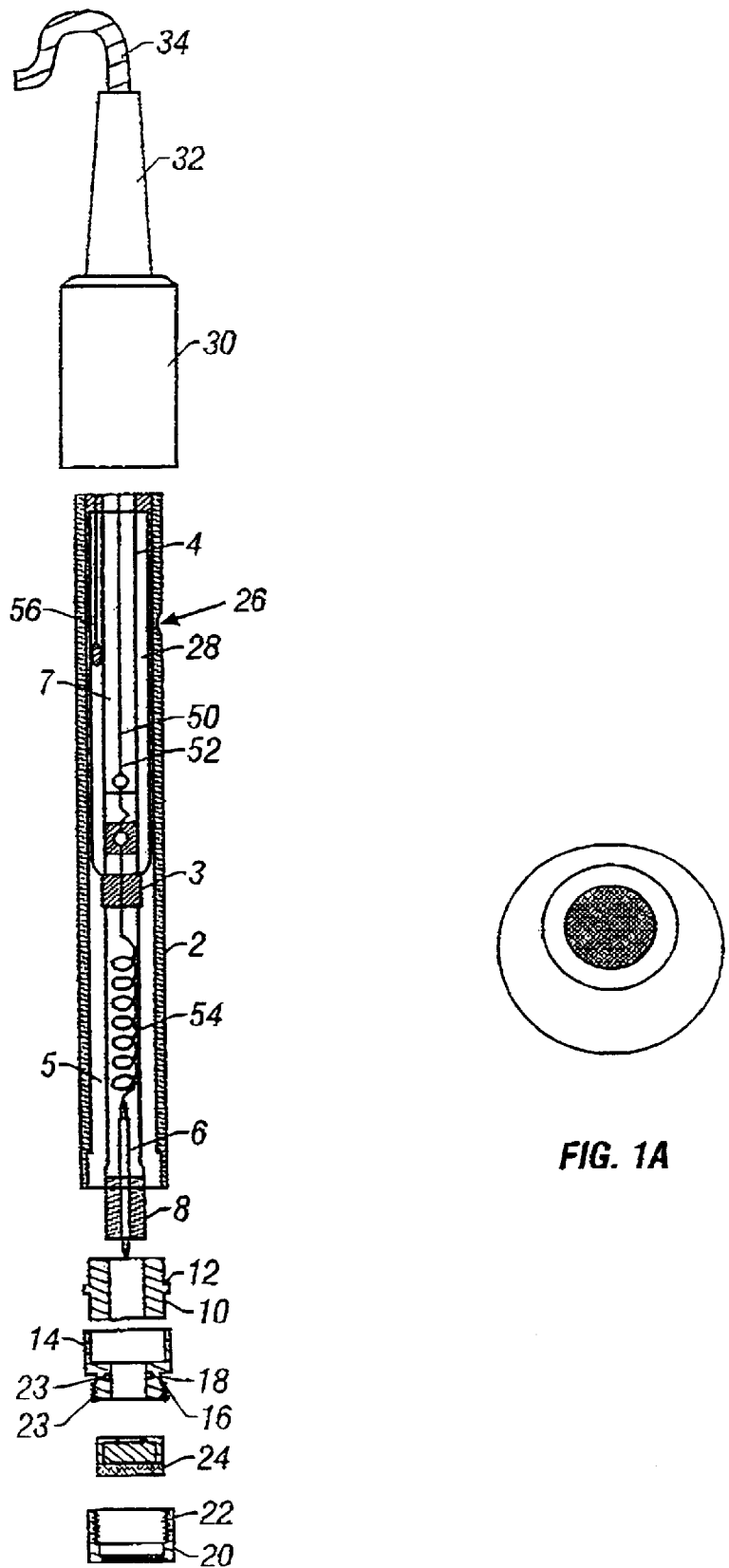
FIG. 1—Cross-sectional exploded side view of one embodiment of the present combination ISE with a replaceable pressed pellet membrane cartridge.
FIG. 1A—Top view of a pressed pellet membrane cartridge of the embodiment of the combination ISE of FIGS. 1 and 2.

Referring to FIG. 1, a cross-sectional exploded side view of one embodiment of the present combination ISE with a replaceable pressed pellet membrane cartridge, main body 2 may be constructed of a chemically resistant plastic, typically an epoxy or DELRIN cylinder threaded to accept membrane cap 20 at the bottom of main body 2. Membrane cap 20 may be constructed of a hollow epoxy or DELRIN chamber with internal threads 22 at the top to mate with cap adapter 14 mounted to main body 2. Fitted within membrane cap 20 is ion-sensitive membrane 24, which in the preferred embodiment comprises a membrane cartridge, selected from the types of membrane materials hereinbefore described and others known in the art, in the preferred embodiment having the form of a PVC cartridge, pressed pellet cartridge, or solid crystal. In an alternative embodiment, membrane 24 is a cartridge, preferably shaped as a disc, i.e., a short cylinder with planer parallel end surfaces, disposed in membrane cap 20 so that it fits tightly, therefore being leak-sealed around its periphery. Its surface is co-planer and resides concentrically in membrane cap 20 and is held in place with at least one O-ring 23 or other suitable structure. O-rings 23 are plastic or rubber or the equivalent, act as sealing rings, and electrically separate the sample from the internal components of the probe. Membrane cartridge 24 is ion-sensitive and connected electrically to an ion-sensing electrode mounted to main body 2, by way of example and not limitation such as an internal filling electrode or solid contact such as spring-loaded pin 6.

Figure 2:
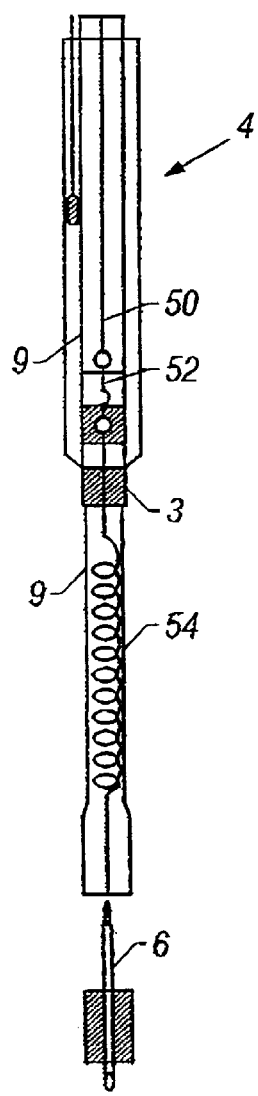
FIG. 2—Cross-sectional side view of the internal body assembly of the present pressed pellet membrane combination ISE.

Referring now to FIG. 2, depicting a presently preferred internal body assembly for use with the present pressed pellet membrane combination ISE, the internal body assembly may vary considerably depending on the construction of reference electrode 4 as discussed hereinafter. In a preferred embodiment described by FIG. 2, reference electrode 4 comprises inner junction 3 as well as other components as discussed subsequently. In a preferred embodiment, inner junction 3 comprises a ceramic material.

As shown in the embodiment described by FIG. 2, first wire 50 is disposed within a center glass tube 9. First wire 50 extends down to junction 3 and is electrically continuous with second wire 52 that is secured in position in glass tube 9 with an appropriate material such as a dollop of silicone. In a preferred embodiment, first wire 50 is a length of 0.010 gauge silver wire and second wire 52 is a platinum wire secured in position in the tube with a dollop of silicone. First wire 50 joins or is otherwise electrically continuous with second wire 52 and extends down tube 9, forming coil 54 and then joining with spring loaded pin 6 and pin bushing 8 at the bottom of reference electrode 4. Additionally, sensing wire referencing element 56 may also be present. Sensing wire referencing element 56 may terminate within reference electrode 4 and may be connected to a secondary reference source located outside reference electrode 4.

Figure 3:
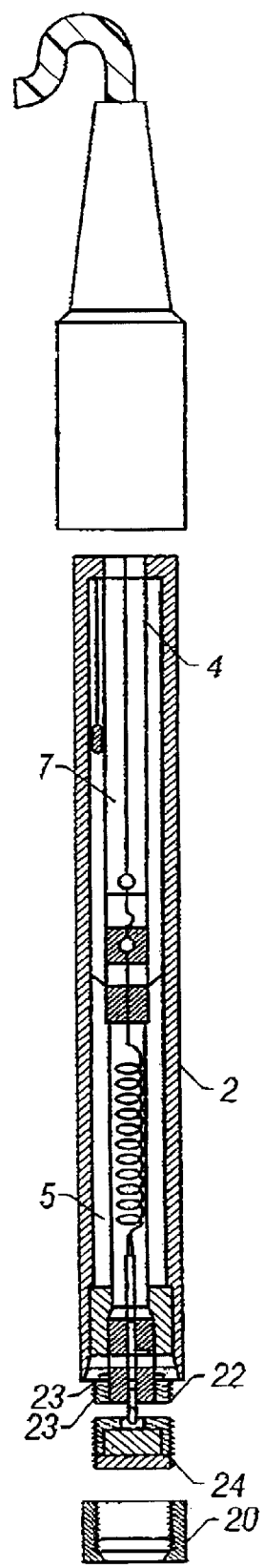
FIG. 3—Cross-sectional side view of one embodiment of the present combination ISE with a replaceable pressed pellet membrane cartridge.

FIG. 3 depicts an embodiment of the present ISE showing membrane cap 20 holding membrane 24 detached from the bottom of main body 2. For this embodiment, reference electrode 4 may use outer reference electrolyte compartment 5 and internal reference electrolyte compartment 7.

Referring back to FIG. 1, in a preferred embodiment, as noted herein above main body 2 houses reference electrode 4. DELRIN is the preferred material from which main body 2 may be formed. Further, reference electrode 4 may have numerous different configurations. The particular construction of reference electrode 4 is not limiting of the invention as the invention is operable with many different types of reference electrode constructions.

Reference electrode 4 may have one or more fill compartments, such as outer reference electrolyte compartment 5 and internal reference electrolyte compartment 7; one or more reference electrolyte compartments 5; one or more ion-permeable junctions 10; and one or more sensing wire referencing elements 56. In a preferred embodiment, inner junction 3 and annular junction 10 are ion-permeable ceramic junctions. Other types of ion-permeable junctions 10 may be used in presently preferred embodiments such as ceramic wicks 10a (not shown in FIG. 1) discussed hereinafter. If reference electrolyte compartment 5 is present, inner junction 3 and annular junction 10 are in communication with reference electrolyte compartment 5 and electrolyte compartment 5 may be externally fillable through fill hole 26. However, in the preferred embodiment, internal reference electrolyte compartment 7 is not externally fillable. It will be understood that there could be additional electrolyte compartments to receive additional reference electrolyte solutions. The present invention can therefore be used with many different types of reference electrodes 4 and is not limited by any particular construction of reference electrode 4. types of reference electrodes 4 and is not limited by any particular construction of reference electrode 4.

Spring-loaded pin 6 is sequestered from reference electrolyte compartment 5 and extends out of the bottom of main body 2 through pin bushing 8.

Ion-permeable junction 10 is disposed around pin bushing 8 in water tight manner. Junction 10 may be sealed around pin bushing 8 with a suitable adhesive such as ARALDITE. In the preferred embodiment, the preferred material for junction 10 comprises ceramic although TEFLON or other porous plastics are suitable.

Junction 10 preferably comprises annular lip 12 on the exterior surface. In a preferred embodiment, annular lip 12 communicates with the sample solution to be tested.

In an alternative embodiment, cap adapter 14 fits over junction 10, engaging annular lip 12 to secure cap adapter 14 on junction 10. Cap adapter 14 may comprise male exterior threads 16 on the bottom portion of cap adapter 14. Cap adapter 14 may also comprise O-ring slot 18 on the bottom surface of cap adapter 14, or otherwise be adapted to accept one or two O-rings 23 disposed between cap adapter 14, membrane cap 20, and membrane 24.

In a preferred embodiment, membrane cap 20 is open at both ends and may preferably be threadedly attached to cap adapter 14, preferably engaging O-ring 23 disposed in slot 18 to form a water tight seal. In a presently preferred embodiment, membrane cap 20 may be partially threaded at the upper portion of membrane cap 20 and may comprise female internal threads 22. Membrane 24 may be disposed within membrane cap 20 at the bottom, unthreaded portion of membrane cap 20.

In the embodiment, referring to FIG. 1 and FIG. 3, membrane 24 comprises a pressed pellet membrane cartridge as shown in FIG. 1A for purposes of illustration.

Although a preferred embodiment comprises male threaded cap adapter 14 mating with female threaded membrane cap 20, an alternative embodiment comprises a female threaded cap adapter 14 mating with a male threaded membrane cap 20. In a further alternative embodiment, cap adapter 14 may be dispensed with in favor of main body 2 being adapted to accept membrane cap 20 directly without the need for cap adapter 14. In yet other alternative embodiments, threaded mating of membrane cap 20 with cap adapter 14 or main body 2 may be replaced with any one, of a variety of suitable connections or combinations thereof, including but not limited to a snap together connection, a pin and groove connection, or simply a suitably tight threadless slide-on connection. Thus, various types of structures can be used for effecting the general design goals described herein.

Also depicted in FIG. 1 is fill hole 26 for introducing a reference electrolyte into annulus 28 between main body 2 and reference electrode 4. Note that the walls of junction 10 seal off the open end of annulus 28 at the bottom of the ISE when junction 10 is properly mounted on pin bushing 8. The apparatus of the present invention is completed with top cap 30, strain relief cap tail 32 extending upward from top cap 30, and cable 34 connecting reference electrode 4 to a suitable read out.

Figures 6, 6A:
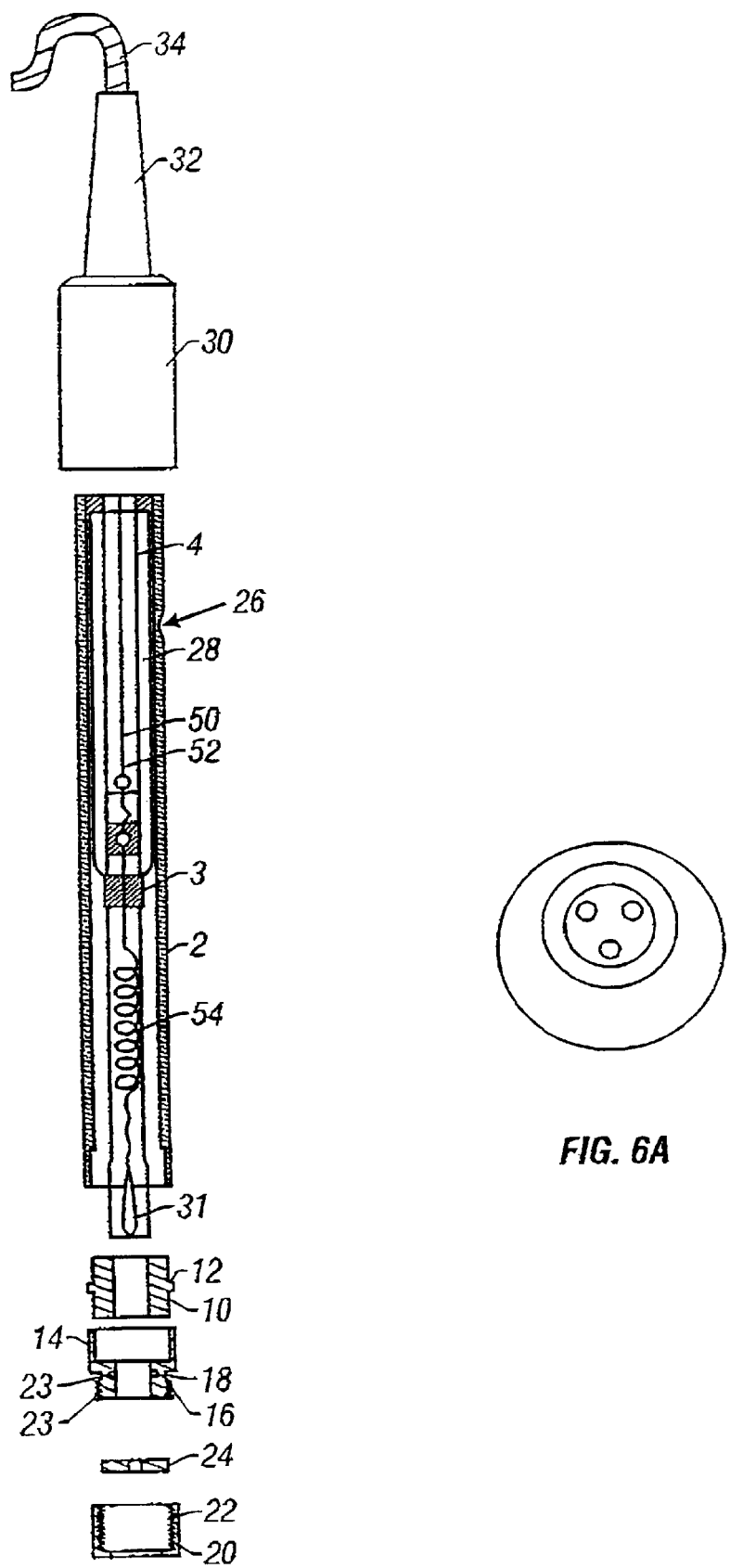
FIG. 6—Cross-sectional exploded side view of the combination ISE of FIG. 5.
FIG. 6A—Top view of a polymer membrane cartridge of the embodiment of the combination ISE of FIGS. 5 and 6.

FIGS. 4, 5, and 6 depict an alternative embodiment of the present ISE, in this instance comprising a PVC cartridge electrode 4 disposed within body 2. In the embodiment of FIGS. 4, 5, and 6, membrane 24 is also a cartridge, preferably comprising a polymer material such as PVC, that will be disposed within membrane cap 20. Membrane 24 is seated abutting the bottom of junction 10 and may be secured in position with membrane cap 20 which may be threaded. Membrane 24 in the embodiment of FIGS. 5 and 6 may preferably comprise a polymer material such as PVC, and may further be perforated, as shown in FIG. 6A. Additionally, reference electrode in FIG. 4 has been modified so that first wire 50, preferably comprising silver, joining the second wire 52, preferably comprising platinum, and extending down the tube in coil 54 terminates in the wire coated or anodized with silver chloride. A suitable internal filling solution 31 may be used to make electrical contact with the silver chloride and membrane 24.

Figures 7, 7A:
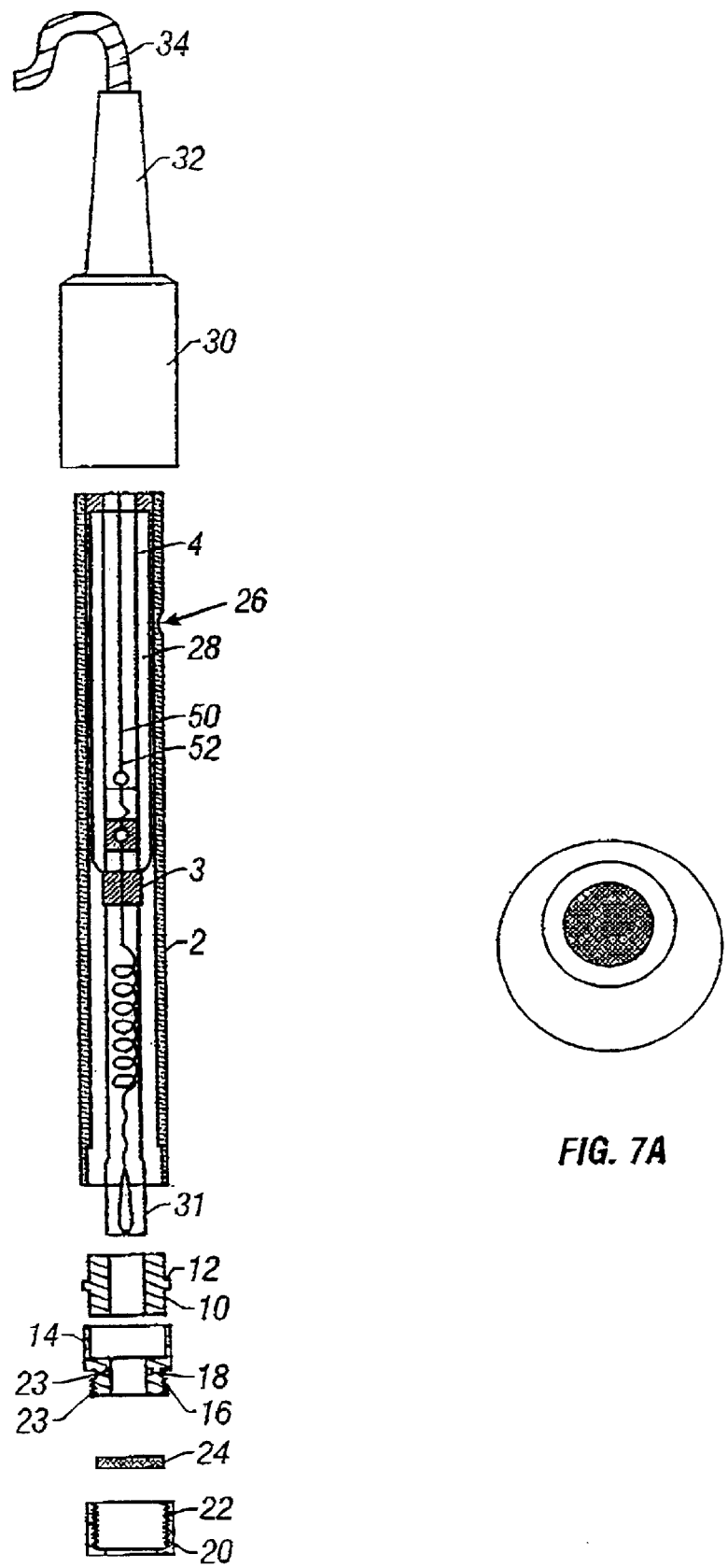
FIG. 7—Cross-sectional exploded side view of an alternative embodiment of the combination ISE of FIGS. 4 and 5, with a replaceable solid crystal membrane.
FIG. 7A—Top view of a solid crystal membrane of the embodiment of the combination ISE of FIG. 7.

FIGS. 7 and 7A depict a further alternative embodiment of the ISE of FIGS. 4, 5, and 6, wherein membrane 24 comprises a solid crystal material instead of a PVC cartridge.

FIGS. 8 and 9 depict an alternative embodiment of the ISE of FIGS. 2, 3, 5, 6, and 7 wherein junction 10, in the preferred embodiment comprising ceramic, is replaced with wick 10a, and cap adapter 14 is modified appropriately. Although the preferred material for wick 10a in this embodiment comprises ceramic, TEFLON or other porous plastics are suitable.

In the operation of the preferred mode, the ISE of the present invention is assembled by seating a selected ion-selective membrane 24 in membrane cap 20, for embodiments such as those of FIGS. 2, 3, 5, and 6, or a solid crystal membrane 24 on the bottom of cap adapter 14, for embodiments such as those of FIGS. 4, 5, and 7. Membrane cap 20 is then threaded onto cap adapter 14. The open end of membrane cap 20 is then exposed to an analytical sample solution. The sample solution develops a voltage/potential across the membrane 24, in accordance with the Nernst equation. Membrane 24 makes electrical contact with internal electrode 4, either by direct contact by electrode 4 in contact with membrane 24 or by filling membrane cap 20 with internal filling solution 31 so that electrode 4 makes an electrical connection with membrane 24. The selected ion may then be detected or measured in the sample solution by observing an appropriate electrical signal.

When membrane cap 20 containing membrane 24 is fully mated with cap adapter 14, O-rings 23 mounted in slot 18 make a seal around the circumference of membrane 24.

One or more electrode kits containing various replaceable membranes 24 may be made available for the analysis of different determinands done on an occasional basis. To replace the membrane 24, membrane cap 20 is removed from the outer body 2, e.g. by unscrewing it in embodiments where membrane cap 20 is threaded, and the old membrane 24, whether cartridge or crystal, is removed from membrane cap 20 by appropriate means such as by pushing membrane 24 out with an appropriate instrument through the open bottom end of membrane cap 20 or otherwise dislodging membrane 24. A new membrane 24 is then inserted into membrane cap 20 by appropriate means such as by pushing membrane 24 until it seats within membrane cap 20. Membrane cap 20 is secured back onto body 2 or to cap adapter 14 mounted on the outer body 2 by appropriate means such as by engaging male and female threads.

By way of example and not limitation, membrane 24 is replaced or exchanged in the embodiment of FIGS. 2, 3, 5, and 6 by unscrewing membrane cap 20 from cap adapter 14 and inserting an appropriate instrument through the open bottom end of membrane cap 20 to dislodge membrane 24 from the interior of cap 20. A new membrane 24 is inserted into cap 20, possibly using the instrument to tap the membrane in to optimal position, and membrane cap 20 secured back onto cap adapter 14. In the embodiment of FIG. 7, membrane cap 20 is removed from cap adapter 14, e.g. by unscrewing membrane cap 20, solid crystal membrane 24 is removed from the bottom of cap adapter 14 and replaced with another solid crystal membrane, and membrane cap 20 secured back onto cap adapter 14.

It may be seen from the preceding description that an improved combination ion-selective electrode with a replaceable ion-sensing membrane has been provided.

It is noted that the embodiment of the combination ion-selective electrode with a replaceable ion-sensing membrane described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A combination ion-selective electrode comprising:
   a removable cap holding an ion-selective membrane wherein a liquid junction is not formed between a reference electrolyte and a sample solution, and wherein said cap and ion-selective membrane may be removed without loss of said reference electrolyte from the combination ion-selective electrode.

2. The ion-selective electrode of claim 1 wherein said ion-selective membrane may be replaceably connected within said cap.

3. The ion-selective electrode of claim 2 wherein said ion-selective membrane is a crystal membrane.

4. The ion-selective electrode of claim 2 wherein said ion-selective membrane is an epoxy membrane.

5. The ion-selective electrode of claim 2 wherein said ion-selective membrane is a pressed pellet membrane.

6. The ion-selective electrode of claim 2 wherein said ion-selective membrane is a polymer membrane.

7. The ion-selective electrode of claim 1 wherein said ion-selective membrane is a crystal membrane.

8. The ion-selective electrode of claim 1 wherein said ion-selective membrane is an epoxy membrane.

9. The ion-selective electrode of claim 1 wherein said ion-selective membrane is a pressed pellet membrane.

10. The ion-selective electrode of claim 1 wherein said ion-selective membrane is a polymer membrane.

11. The ion-selective electrode of claim 1 wherein said cap is removably connected to an ion-permeable junction member.

12. The ion-selective electrode of claim 11 wherein said ion-permeable junction member is formed of ceramic.

13. A combination ion-selective electrode comprising:

an electrode body having a reference half-cell including a reference electrolyte;

an ion-permeable junction connected to said electrode body;

an ion-selective electrode disposed through said ion-permeable junction in a manner such that a liquid junction is not formed between said reference electrolyte and a sample solution; and an ion-selective membrane removably connected to said ion-permeable junction without loss or contamination of said reference electrolyte, said ion-selective membrane in functional connection with said ion-selective electrode.

14. The ion-selective electrode of claim 13 wherein said ion-selective electrode is spring loaded for urging said electrode in functional connection with said ion-selective membrane.

15. The ion-selective electrode of claim 13 wherein said ion-selective electrode is functionally connected to said ion-selective membrane via a filling solution.

16. The ion-selective electrode of claim 13 wherein said ion-selective electrode is held by a cap removably connected to said ion-permeable junction.

17. The ion-selective electrode of claim 16 wherein said ion-selective electrode is replaceably connected to said cap.

18. The ion-selective electrode of claim 17 wherein said ion-selective electrode is spring loaded for functionally connecting to said ion-selective membrane.

19. The ion-selective electrode of claim 17 wherein said ion-selective electrode is functionally connected to said ion-selective membrane via a filling solution.

20. The ion-selective electrode of claim 16 wherein said ion-selective electrode is spring loaded for functionally connecting to said ion-selective membrane.

21. The ion-selective electrode of claim 16 wherein said ion-selective electrode is functionally connected to said ion-selective membrane via a filling solution.

22. A combination ion-selective electrode comprising:

an electrode body having a reference half-cell including a reference electrolyte;

an ion-permeable junction connected to said electrode body;

an ion-selective electrode disposed through said ion-permeable junction in a manner to prevent fluid from escaping from said electrode body and not form a liquid junction between said reference electrolyte and a sample solution; and an ion-selective membrane removably connected to said ion-permeable junction without loss or contamination of said reference electrolyte, said ion-selective membrane in functional connection with said ion-selective electrode.

23. The ion-selective electrode of claim 22 wherein said ion-selective electrode is spring loaded for urging said electrode in functional connection with said ion-selective membrane.

24. The ion-selective electrode of claim 22 wherein said ion-selective electrode is functionally connected to said ion-selective membrane via a filling solution.

25. The ion-selective electrode of claim 22 wherein said ion-selective electrode is held by a cap removably connected to said ion-permeable junction.

26. The ion-selective electrode of claim 25 wherein said ion-selective electrode is replaceably connected to said cap.

27. The ion-selective electrode of claim 26 wherein said ion-selective electrode is spring loaded for functionally connecting to said ion-selective membrane.

28. The ion-selective electrode of claim 26 wherein said ion-selective electrode is functionally connected to said ion-selective membrane via a filling solution.

29. The ion-selective electrode of claim 25 wherein said ion-selective electrode is spring loaded for functionally connecting to said ion-selective membrane.

30. The ion-selective electrode of claim 25 wherein said ion-selective electrode is functionally connected to said ion-selective membrane via a filling solution.

31. A combination ion-selective electrode comprising:

an electrode body having a reference half-cell including a reference electrolyte;

an ion-permeable junction connected to said electrode body;

an ion-selective electrode disposed through said ion-permeable junction in a manner to prevent fluid from escaping from said electrode body and not form a liquid junction between said reference electrolyte and a sample solution; and a cap holding a replaceable ion-selective membrane, said cap removably connected to said ion-permeable junction without loss or contamination of said reference electrolyte, said ion-selective membrane in functional connection with said ion-selective electrode.

32. The ion-selective electrode of claim 31 wherein said ion-selective electrode is spring loaded for urging said electrode in functional connection with said ion-selective membrane.

33. The ion-selective electrode of claim 31 wherein said ion-selective electrode is functionally connected to said ion-selective membrane via a filling solution.

* * * * *